United States Patent

Hoffmann et al.

[11] 4,001,404
[45] Jan. 4, 1977

[54] N-DITHIOPHOSPHORYL-CARBAMIC ACID ESTERS

[75] Inventors: Hellmut Hoffmann, Wuppertal; Wolfgang Behrenz, Overath-Steinenbrueck; Ingeborg Hammann, Cologne; Bernhard Homeyer, Opladen, all of Germany

[73] Assignee: Bayer Aktiengesellschaft, Leverkusen, Germany

[22] Filed: June 20, 1975

[21] Appl. No.: 588,921

[30] Foreign Application Priority Data

July 2, 1974  Germany ............................ 2431849

[52] U.S. Cl. .............................. 424/212; 260/938; 260/939
[51] Int. Cl.² ....................... A01N 9/36; C07F 9/24
[58] Field of Search ..................... 260/938; 424/212

[56] References Cited
UNITED STATES PATENTS 3,887,657   6/1975   Battershell et al. ............... 260/938

*Primary Examiner*—Anton H. Sutto
*Attorney, Agent, or Firm*—Burgess, Dinklage & Sprung

[57] ABSTRACT

N-Dithiophosphoryl-carbamic acid esters of the formula

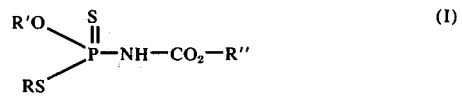

in which
R and R' each independently is alkyl with 1 to 6 carbon atoms, and
R'' is alkyl with 1 to 6 carbon atoms, halogenoalkyl with 1 to 4 carbon atoms or dialkylaminoalkyl with 1 to 4 carbon atoms in each alkyl moiety,
which possess insecticidal and acaricidal properties.

9 Claims, No Drawings

N-DITHIOPHOSPHORYL-CARBAMIC ACID ESTERS

The present invention relates to and has for its object the provision of particular new N-dithiophosphoryl-carbamic acid esters, i.e. N-(alkoxyalkylmercapto-thiophosphoryl)-carbamic acid alkyl, halogenoalkyl or dialkylaminoalkyl esters, which possess insecticidal and acaricidal properties, active compositions in the form of mixtures of such compounds with solid and liquid dispersible carrier vehicles, and methods for producing such compounds and for using such compounds in a new way especially for combating pests, e.g., insects and acarids, with other and further objects becoming apparent from a study of the within specification and accompanying examples.

It is known from German Published Specification DOS No. 1,793,118 that O,S-dialkyldithiophosphoric acid ester-amides, for example O,S-dimethyl- (Compound A), O,S-diethyl- (Compound B), S-methyl-O-n-butyl-(Compound C) and S-methyl-O-n-pentyl-thiol-thiono-phosphoric acid diesteramides (Compound D), possess insecticidal and acaricidal properties.

The present invention provides, as new compounds, the N-dithiophosphoryl-carbamic acid esters of the general formula

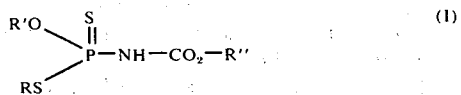

in which
R and R' each independently is alkyl with 1 to 6 carbon atoms, and
R'' is alkyl with 1 to 6 carbon atoms, halogenoalkyl with 1 to 4 carbon atoms or dialkylaminoalkyl with 1 to 4 carbon atoms in each alkyl moiety.

Preferably R and R', which may be identical or different, are each straight-chain or branched alkyl with 1 to 4 carbon atoms and R'' is straight-chain or branched alkyl with 1 to 3 carbon atoms, halogenoalkyl with 1 to 3 carbon atoms or dialkylaminoalkyl with 1 to 3 carbon atoms in each alkyl moiety.

Surprisingly, the N-dithiophosphoryl-carbamic acid esters according to the invention exhibit a better insecticidal and acaricidal action than the compounds of analogous structure and of the same type of action previously known from the state of the art. The compounds according to the invention thus represent a genuine enrichment of the art.

The present invention also provides a process for the preparation of an N-dithiophosphoryl-carbamic acid ester of the formula (I) in which a dithiophosphoryl isocyanate of the general formula

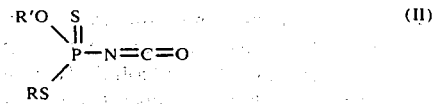

in which
R and R' have the above-mentioned meanings. is reacted with a hydroxy derivative of the general formula

HO—R''                         (III)

in which
R'' has the above-mentioned meaning, optionally in the presence of a solvent or diluent.

If, for example, O,S-di-n-propyl-thionothiolphosphoric acid diester isocyanate and tert.-butanol are used as the starting materials, the course of the reaction can be represented by the following equation:

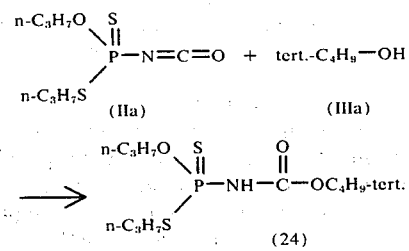

The dithiophosphoryl isocyanates (II) to be used as starting materials have not been described in the literature but can be prepared according to customary processes by reacting the known O,S-dialkyl-dithiophosphoric acid diesteramides (shown in German Published Specification DOS No. 1,793,118) with phosgene.

The following may be mentioned as examples of such isocyanates: O,S-dimethyl-, O,S-diethyl-, O,S-di-n-propyl-, O,S-di-isopropyl-, O,S-di-n-butyl-, O,S-di-sec.-butyl, O,S-di-isobutyl-, O,S-di-tert.-butyl-, O-methyl-S-ethyl-, O-ethyl-S-n-propyl-, O-ethyl-S-isopropyl-, O-ethyl-S-n-butyl-, O-ethyl-S-sec.-butyl-, O-n-propyl-S-ethyl- or O-n-butyl-S-ethyl-thionothiol-phosphoric acid diester isocyanate.

The hydroxy derivatives (III) used as starting materials are already known. The following may be mentioned as examples: methanol, ethanol, n- or isopropanol, 2-chloroethan-1-ol, 1,3-dichloropropan-2-ol, 2,2,2-trichloroethanol, 2-dimethylaminoethanol, 2-diethylaminoethanol or 1-dimethylaminopropan-2-ol.

All inert organic solvents may be used as solvents or diluents for the reaction according to the invention, especially aliphatic and aromatic, optionally chlorinated, hydrocarbons, such as benzene, toluene, xylene, benzine, methylene chloride, chloroform, carbon tetrachloride or chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

The reaction temperature can be varied within a fairly wide range. In general, the reaction is carried out at between 0° and 100° C, preferably at from 15° to 50° C.

The reaction is in general carried out under normal pressure.

In carrying out the process according to the invention, the hydroxy compound is in most cases employed in 10 to 20% excess. The reaction is preferably carried out in the presence of one of the above-mentioned solvents, at the stated temperatures. The reaction mixture is then worked up in the usual manner, for example by filtration and evaporation of the solvent.

The new compounds are obtained in the form of oils, which in most cases be distilled without decomposition, but are freed from the last volatile constituents by so-called "slight distillation", that is to say by prolonged heating under reduced pressure to moderately elevated temperatures, and are purified in this way. They are characterized by the refractive index.

As has already been mentioned, the N-dithiophosphorylcarbamic acid esters according to the invention are distinguished by an excellent insecticidal and acaricidal activity. They are active not only against leaf insects and soil insects and mites, but also against pests harmful to health and pests of stored products. They combine a low phytotoxicity with a good action against sucking and biting insects and mites.

For this reason, the compounds according to the invention can be employed successfully as pesticides in plant protection and in the hygiene field and field of protection of stored products.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly caterpillars (Lepidoptera) such as the diamond-back moth (*Plutella maculipennis*), the gypsy moth (*Lymantria dispar*), the browntail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (Ephestia kuhniella) and greater wax moth (*Galleria mellonella*).

Also to be classed with the biting insects are beetles (Coleoptera), for example the granary weevil (*Sitophilus granarius* = *Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (*Bruchidius* = *Acanthoscelides obtectus*), the leather beetle (*Dermestes frischi*), the khapra beetle (*Trogoderma granarium*), the flour beetle (*Tribolium castaneum*), the northern corn billbug (Calandra or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (Agriotes spec.) and larvae of the cockchafer (*Melolontha melolontha*); cockroaches, such as the German cockroach (*Blattella germanica*), American cockroach (*Periplaneta americana*), Madeira cockroach (Leucophaea or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (Acarina) there are classed, in particular, the spider mites (Tetranychidae) such as the twospotted spider mite (*Tetranychus urticae*) and the European red mite (*Paratetranychus pilosus* = *Panonychus ulmi*), gall mites, for example the blackcurrant gall mite (*Eriophyes ribis*) and tarsonemids, for example the broad mite (*Hemitarsonemus latus*) and the cylamen mite (*Tarsonemus pallidus*); finally, ticks, such as the relapsing fever tick (*Ornithodorus moubata*).

When applied against pests and pests of stored products, particularly flies and mosquitoes, the present compounds are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders of the type usable in conventional pesticide formulations or compositions, e.g., conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g., conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other nematocides, insecticides, acaricides and fungicides, or bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority ad outstanding activity of the particular new compounds of the present invention are illustrated, without limitation, by the following examples:

EXAMPLE 1

Critical concentration test/soil insects
Test insect: *Tenebrio molitor* larvae
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted in ppm (= mg/1). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness was 100% if all test insects had been killed and was 0% if exactly as many test insects were still alive as in the case of the untreated control.

The active compounds, amounts used and results can be seen from the table which follows:

Table 1

Critical concentration test/soil insects
(*Tenebrio molitor* larvae)

| Active compound | Degree of destruction in % at an active compound concentration of 40 ppm |
|---|---|
| $\begin{array}{c}CH_3O\phantom{xxx}S\\ \phantom{xx}\diagdown\|\phantom{x}\\ \phantom{xxxx}P-NH_2\\ \phantom{xx}\diagup\\ CH_3S\end{array}$ (A) | 0 |

Table 1-continued

Critical concentration test/soil insects
(*Tenebrio molitor* larvae)

| Active compound | Degree of destruction in % at an active compound concentration of 40 ppm |
|---|---|
| $\begin{array}{c} C_2H_5O \\ \phantom{C_2H_5O}\diagdown\|\\ \phantom{C_2H_5O}\phantom{\diagdown}P-NH-CO_2-C_3H_7\text{-iso} \\ \phantom{C_2H_5O}\diagup \\ n\text{-}C_3H_7S \end{array}$ (4) | 100 |
| $\begin{array}{c} n\text{-}C_3H_7S \\ \phantom{n\text{-}C_3H_7S}\diagdown\|\phantom{xx}\| \\ \phantom{n\text{-}C_3H_7S}\phantom{\diagdown}P-NH-C-OC_2H_5 \\ \phantom{n\text{-}C_3H_7S}\diagup \\ CH_3O \end{array}$ (1) | 100 |
| $\begin{array}{c} n\text{-}C_3H_7S \\ \diagdown\|\phantom{xx}\| \\ P-NH-C-OC_3H_7\text{-iso} \\ \diagup \\ CH_3O \end{array}$ (9) | 100 |
| $\begin{array}{c} n\text{-}C_3H_7S \\ \diagdown\|\phantom{xx}\| \\ P-NH-C-OCH_3 \\ \diagup \\ CH_3O \end{array}$ (16) | 100 |

EXAMPLE 2

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the two-spotted spider mite (*Tetranychus urticae*) in all stages of development.

After the specified periods of time, the degree of destruction was determined as a percentage: 100% means that all the spider mites were killed whereas 0% means that none of the spider mites were killed.

The active compounds, the concentrations of the active compounds, the evaluation times and the results can be seen from the following table:

Table 2

(*Tetranychus* test/resistant)
Active Compound Concentration = 0.1%

| Active Compound | Degree of destruction in % after 2 days |
|---|---|
| $\begin{array}{c} CH_3O \\ \diagdown\| \\ P-NH_2 \\ \diagup \\ CH_3S \end{array}$ (A) | 0 |
| $\begin{array}{c} n\text{-}C_3H_7S \\ \diagdown\|\phantom{xx}\| \\ P-NH-C-OCH_3 \\ \diagup \\ CH_3O \end{array}$ (16) | 100 |

Table 2-continued (*Tetranychus* test/resistant)
Active Compound Concentration = 0.1%

| Active Compound | Degree of destruction in % after 2 days |
|---|---|
| $\begin{array}{c} n\text{-}C_3H_7S \\ \diagdown\|\phantom{xx}\| \\ P-NH-C-OCH_3 \\ \diagup \\ C_2H_5O \end{array}$ (12) | 100 |
| $\begin{array}{c} n\text{-}C_3H_7S \\ \diagdown\|\phantom{xx}\| \\ P-NH-C-OC_2H_5 \\ \diagup \\ CH_3O \end{array}$ (1) | 100 |
| $\begin{array}{c} n\text{-}C_3H_7S \\ \diagdown\|\phantom{xx}\| \\ P-NH-C-OC_2H_5 \\ \diagup \\ C_2H_5O \end{array}$ (10) | 100 |
| $\begin{array}{c} CH_3O \\ \diagdown\| \\ P-NH-CO_2-C_2H_5 \\ \diagup \\ n\text{-}C_4H_9S \end{array}$ (8) | 100 |
| $\begin{array}{c} C_2H_5O \\ \diagdown\| \\ P-NH-CO_2-C_2H_5 \\ \diagup \\ n\text{-}C_4H_9S \end{array}$ (6) | 98 |
| $\begin{array}{c} n\text{-}C_3H_7S \\ \diagdown\|\phantom{xx}\| \\ P-NH-C-OC_3H_7\text{-iso} \\ \diagup \\ CH_3O \end{array}$ (9) | 100 |
| $\begin{array}{c} C_2H_5O \\ \diagdown\| \\ P-NH-CO_2-C_3H_7\text{-iso} \\ \diagup \\ n\text{-}C_3H_7S \end{array}$ (4) | 100 |
| $\begin{array}{c} CH_3O \\ \diagdown\| \\ P-NH-CO_2-C_3H_7\text{-iso} \\ \diagup \\ n\text{-}C_4H_9S \end{array}$ (5) | 99 |

EXAMPLE 3

Phaedon larvae test
Solvent: 3 parts by weight of acetone
Emulsifier: 1 part by weight alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) were sprayed with the preparation of the active compound until dripping wet and were then infested with mustard beetle larvae (*Phaedon cochleariae*).

After the specified periods of time, the degree of destruction was determined in %: 100% means that all beetle larvae had been killed whereas 0% means that none of the beetle larvae had been killed.

The active compounds, the concentrations of the active compounds, the evaluation times and the results can be seen from the following table:

Table 3

(Phaedon larvae test)
Active Compound Concentration = 0.01%

| Active Compound | Degree of destruction in % after 3 days |
|---|---|
| n-C$_4$H$_9$O\P(=S)-NH$_2$ / CH$_3$S  (C) | 0 |
| n-C$_5$H$_{11}$O\P(=S)-NH$_2$ / CH$_3$S  (D) | 10 |
| C$_2$H$_5$O\P(=S)-NH$_2$ / C$_2$H$_5$S  (B) | 0 |
| n-C$_3$H$_7$S\P(=S)-NH-C(=O)-OCH$_3$ / CH$_3$O  (16) | 100 |
| n-C$_3$H$_7$S\P(=S)-NH-C(=O)-OCH$_3$ / C$_2$H$_5$O  (12) | 100 |
| n-C$_3$H$_7$S\P(=S)-NH-C(=O)-OC$_2$H$_5$ / C$_2$H$_5$O  (10) | 100 |
| n-C$_3$H$_7$S\P(=S)-NH-C(=O)-OC$_3$H$_7$-iso / CH$_3$O  (9) | 100 |

Table 4

(Sitophilus granarius test)

| Active compound | Active compound concentrations of the solution in % | Degree of destruction in % |
|---|---|---|
| CH$_3$O\P(=S)-NH$_2$ / CH$_3$S  (A) | 0.2 / 0.02 | 100 / 0 |
| n-C$_3$H$_7$S\P(=S)-NH-C(=O)-OCH$_3$ / C$_2$H$_5$O  (12) | 0.02 | 100 |
| n-C$_3$H$_7$S\P(=S)-NH-C(=O)-OC$_2$H$_5$ / C$_2$H$_5$O  (10) | 0.02 | 100 |
| C$_2$H$_5$O\P(=S)-NH-CO$_2$-C$_3$H$_7$-iso / n-C$_3$H$_7$S  (4) | 0.02 | 100 |
| n-C$_3$H$_7$S\P(=S)-NH-C(=O)-OC$_3$H$_7$-iso / CH$_3$O  (9) | 0.02 | 80 |
| n-C$_3$H$_7$S\P(=S)-NH-C(=O)-OCH$_3$ / CH$_3$O | 0.02 | 100 |
| CH$_3$O\P(=S)-NH-CO$_2$-C$_2$H$_5$ / n-C$_4$H$_9$S | 0.02 | 80 |

EXAMPLE 4

Test insects: *Sitophilus granarius*
Solvent: Acetone 2 parts by weight of the active compound were taken up in 1,000 parts by volume of the solvent. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per m$^2$ of filter paper varied with the concentration of the solution of active compound. About 25 test insects were then placed in the Petri dish and it was covered with a glass lid.

The condition of the test insects was observed 3 days after the commencement of the experiments. The destruction, in %, was determined. 100% denotes that all test insects had been killed; 0% denotes that no test insects had been killed.

The active compounds, the concentrations of the active compounds and the results can be seen from the following table:

EXAMPLE 5 a. The dithiophosphoryl isocyanates (II) which were used as starting materials were prepared, for example, as follows:

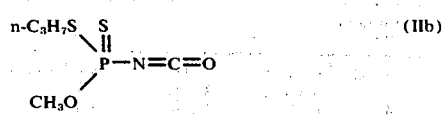
(IIb)

A mixture of 111 g of O-methyl-S-n-propylthionothiolphosphoric acid diester-amide, 97 g of pyridine and 1,000 ml of toluene was added to 66 g (0.6 mole) of phosgene in 350 ml of toluene at −70° C. The mixture was stirred for 1 hour at −60° to −40° C. The temperature was then allowed to rise to 20° C over the course of 2 hours, the solids which had separated out were filtered off and the solvent was evaporated off. The residue was distilled at 105° C/2 mm Hg and 30 g (24% of theory) of O-methyl-S-n-propyl-thionothiolphosphoric acid diester isocyanate were thus obtained.

The following additional starting materials could be prepared analogously:

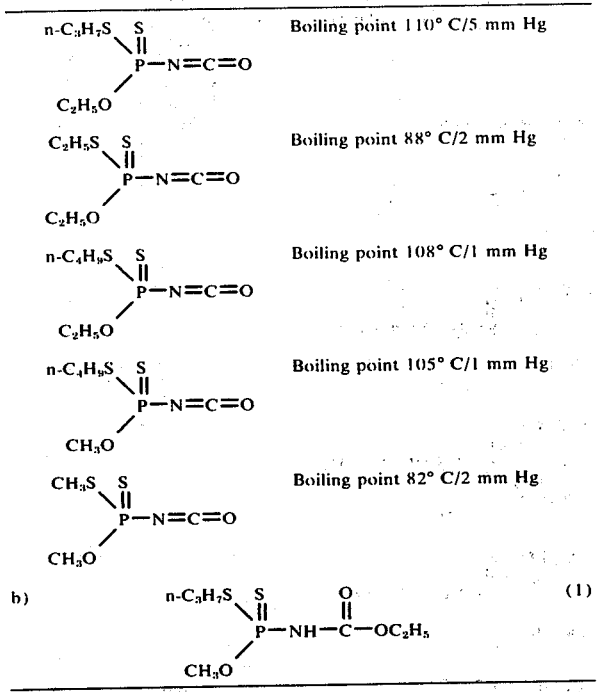

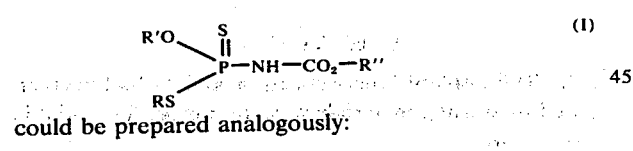

3 g (0.06 mole) of ethanol were added dropwise to 11 g (0.05 mole) of O-methyl-S-n-propyl-thionothiolphosphoric acid diester isocyanate in 20 ml of toluene, whereupon the reaction temperature rose to 35° C. The reaction mixture was left to stand for 3 hours and was filtered through kieselguhr, and the solvent was distilled off in vacuo. The residue was subjected to slight distillation and 11 g (86% of theory) of N-(methoxy-n-propylmercapto-thiophosphoryl)-carbamic acid ethyl ester having a refractive index $n_D^{21}$ of 1.5391 were obtained.

The following compounds of the general formula

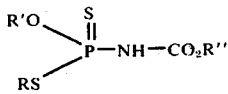 (I)

could be prepared analogously:

| Compound No. | R | R' | R'' | Refractive index |
|---|---|---|---|---|
| 2 | $C_2H_5$ | $C_2H_5$ | $C_3H_7$-iso | $n_D^{22} = 1.5134$ |
| 3 | n-$C_4H_9$ | $C_2H_5$ | $CH_3$ | $n_D^{21} = 1.5222$ |
| 4 | n-$C_3H_7$ | $C_2H_5$ | $C_3H_7$-iso | $n_D^{22} = 1.5099$ |
| 5 | n-$C_4H_9$ | $CH_3$ | $C_3H_7$-iso | $n_D^{21} = 1.5159$ |
| 6 | n-$C_4H_9$ | $C_2H_5$ | $C_2H_5$ | $n_D^{22} = 1.5150$ |
| 7 | n-$C_3H_7$ | $C_2H_5$ | $-CH_2CH_2N(C_2H_5)_2$ | $n_D^{22} = 1.5308$ |
| 8 | n-$C_3H_7$ | $CH_3$ | $C_2H_5$ | $n_D^{21} = 1.5241$ |
| 9 | n-$C_3H_7$ | $CH_3$ | $C_3H_7$-iso | $n_D^{21} = 1.5300$ |
| 10 | n-$C_3H_7$ | $C_2H_5$ | $C_2H_5$ | $n_D^{24} = 1.5162$ |
| 11 | n-$C_3H_7$ | $C_2H_5$ | $-CH_2-CCl_3$ | $n_D^{22} = 1.5359$ |
| 12 | n-$C_3H_7$ | $C_2H_5$ | $CH_3$ | $n_D^{24} = 1.5259$ |
| 13 | $C_2H_5$ | $C_2H_5$ | $C_2H_5$ | $n_D^{22} = 1.5230$ |
| 14 | $CH_3$ | $CH_3$ | $C_3H_7$-iso | $n_D^{22} = 1.5294$ |
| 15 | $C_2H_5$ | $C_2H_5$ | $CH_3$ | $n_D^{22} = 1.5330$ |
| 16 | n-$C_3H_7$ | $CH_3$ | $CH_3$ | $n_D^{21} = 1.5440$ |
| 17 | $CH_3$ | $CH_3$ | $C_2H_5$ | $n_D^{22} = 1.5417$ |
| 18 | $CH_3$ | $CH_3$ | $CH_3$ | $n_D^{22} = 1.5551$ |
| 19 | $CH_3$ | sec-$C_4H_9$ | n-$C_3H_7$ | |
| 20 | $C_2H_5$ | $C_3H_7$-iso | $-CH_2-Cl$ | |
| 21 | n-$C_3H_7$ | $C_2H_5$ | $-CH_2N$ (n-$C_3H_7)_2$ | |
| 22 | $C_3H_7$-iso | $C_2H_5$ | $-CH_2-CH(CH_3)N(CH_3)_2$ | |
| 23 | n-$C_3H_7$ | n-$C_4H_9$ | $-CH_2-CHBr-CH_2Br$ | |

It will be appreciated that the instant specification and examples are set forth by way of illustration and not limitation, and that various modifications and changes may be made without departing from the spirit and scope of the present invention.

What is claimed is:

1. An N-dithiophosphoryl-carbamic acid ester of the formula

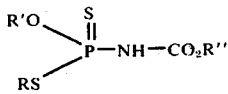

in which
R and R' each independently is alkyl with 1 to 6 carbon atoms, and
R'' is alkyl with 1 to 6 carbon atoms, halogenoalkyl with 1 to 4 carbon atoms or dialkylaminoalkyl with 1 to 4 carbon atoms in each alkyl moiety.

2. A compound according to claim 1, in which R and R' each is alkyl with 1 to 4 carbon atoms, and R''' is alkyl with 1 to 3 carbon atoms, halogenoalkyl with 1 to 3 carbon atoms or dialkylaminoalkyl with 1 to 3 carbon atoms in each alkyl moiety.

3. The compound according to claim 1 wherein such compound is N-(methoxy-n-propylmercapto-thiophosphoryl)-carbamic acid isopropyl ester of the formula

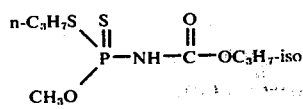

4. The compound according to claim 1 wherein such compound is N-(ethoxy-n-propylmercapto-thiophosphoryl)-carbamic acid ethyl ester of the formula

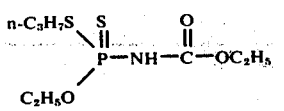

5. The compound according to claim 1 wherein such compound is N-(ethoxy-n-propylmercapto-thiophosphoryl)-carbamic acid methyl ester of the formula

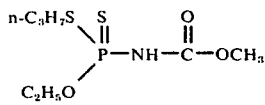

6. The compound according to claim 1 wherein such compound is N-(methoxy-n-propylmercapto-thiosphosphoryl)-carbamic acid methyl ester of the formula

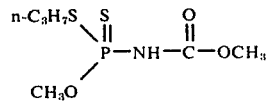

7. An insecticidal or acaricidal composition containing as active ingredient an insecticidally or acaricidally effective amount of a compound according to claim 1 in admixture with a diluent.

8. A method of combating insects or acarids which comprises applying to the insects or acarids or to a habitat thereof an insecticidally or acaricidally effective amount of a compound according to claim 1.

9. The method according to claim 8 wherein such compound is
N-(methoxy-n-propylmercapto-thiophosphoryl)-carbamic acid isopropyl ester,
N-(ethoxy-n-propylmercapto-thiophosphoryl)-carbamic acid ethyl ester,
N-(ethoxy-n-propylmercapto-thiophosphoryl)-carbamic acid methyl ester, or
N-(methoxy-n-propylmercapto-thiophosphoryl)-carbamic acid methyl ester.

* * * * *